US012758113B2

(12) United States Patent
Yu et al.

(10) Patent No.: US 12,758,113 B2
(45) Date of Patent: Oct. 13, 2026

(54) ESC EVALUATION METHOD

(71) Applicant: Withings, Issy les Moulineaux (FR)

(72) Inventors: Roger Yu, Issy les Moulineaux (FR); Brice Brac De La Perriere, Issy les Moulineaux (FR); Jérôme Bredin, Issy les Moulineaux (FR); Antoine Merlot, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 366 days.

(21) Appl. No.: 18/523,301

(22) Filed: Nov. 29, 2023

(65) Prior Publication Data

US 2024/0180441 A1 Jun. 6, 2024

(30) Foreign Application Priority Data

Dec. 5, 2022 (EP) .................................... 22315305

(51) Int. Cl.

| | |
|---|---|
| ***A61B 5/0531*** | (2021.01) |
| ***A61B 5/00*** | (2006.01) |
| ***A61B 5/0533*** | (2021.01) |
| ***A61B 5/0537*** | (2021.01) |

(52) U.S. Cl.

CPC .......... *A61B 5/0531* (2013.01); *A61B 5/0533* (2013.01); *A61B 5/0537* (2013.01); *A61B 5/6887* (2013.01); *A61B 2560/0223* (2013.01)

(58) Field of Classification Search

CPC ... A61B 5/0531; A61B 5/0533; A61B 5/0537; A61B 5/6887; A61B 2560/0223; A61B 5/14532

See application file for complete search history.

(56) References Cited

U.S. PATENT DOCUMENTS

2010/0274113 A1* 10/2010 Brunswick ........... A61B 5/6825 600/372
2014/0350432 A1* 11/2014 Khalfallah ........... A61B 5/4076 600/547
2018/0085036 A1* 3/2018 Bocquet ............... A61B 5/0531

(Continued)

FOREIGN PATENT DOCUMENTS

FR 3 131 521 A1 7/2023
WO WO 2006/136598 A2 12/2006
WO WO 2008/107324 A1 9/2008

(Continued)

OTHER PUBLICATIONS

Extended European Search Report as issued in French Patent Application No. 22315305.7, dated Feb. 22, 2023.

*Primary Examiner* — Jason M Sims
*Assistant Examiner* — Kyle W. Kretzer
(74) *Attorney, Agent, or Firm* — CUSHMAN PARTNERS, LLC

(57) ABSTRACT

A method to evaluate an electrochemical skin conductance (ESC) of a user body using a measurement device, the measurement device including a pair of electrodes including an anode and a cathode, a direct voltage source, a measurement resistor, control circuitry configured to set the electrical resistance value of the measurement resistor and to set the value of the direct voltage, wherein the method includes, by the control circuitry pre-stabilizing during a pre-stabilizing period, measuring during a measurement period following the pre-stabilization period.

18 Claims, 8 Drawing Sheets

(56) References Cited

U.S. PATENT DOCUMENTS

2019/0046064 A1* 2/2019 Centen .................. A61B 5/282

FOREIGN PATENT DOCUMENTS

| | | | |
|---|---|---|---|
| WO | WO 2013/075963 | A1 | 5/2013 |
| WO | WO 2014/033105 | A1 | 3/2014 |
| WO | WO 2015/036530 | A1 | 3/2015 |
| WO | WO 2016/083432 | A1 | 6/2016 |

* cited by examiner

ESC EVALUATION METHOD

CROSS-REFERENCE TO RELATED APPLICATIONS

This application claims priority to European Patent Application No. 22315305.7, filed Dec. 5, 2022, the entire content of which is incorporated herein by reference in its entirety.

FIELD

The present disclosure relates to devices configured to measure an electrochemical sudoral skin (ESC) response of a user. Such ESC measurements enable to estimate a neurologic state of the user. More particularly, the present disclosure relates to such devices that may be used at home, on a regular basis, notably bathroom scales.

Documents WO2006/136598, WO2008/107324, WO2013/075963, WO2014/033105, WO2015/036530 WO2016/083432 (called hereinafter the "sudoscan documents") describe a system allowing such an ESC evaluation.

BACKGROUND

The ESC typically includes applying, at a pair of electrodes in contact with the human body (e.g., two feet) a direct voltage at an anode and measuring a voltage at a cathode to determine a current going through the body using a measurement resistor.

In that regard, the sudoscan documents disclose the following method: a calibration step, during which a measurement resistor is calibrated at an appropriate value for the ESC measurement, followed by the measurement step, in which different steps of direct voltage are applied to the electrodes. A step may last between 0.1 s and 5 s. Each step includes a stabilization period (see for instance document US20140350432) before actually using the measured voltage value of the cathode to determine an ESC value. The stabilization period is long enough to allow the stabilization of electrochemical phenomena in the body in the vicinity of the electrode.

However, those stabilization periods increase the duration of the measure. This is acceptable in a hospital environment, where the time constraint is not particularly relevant. Conversely, for a device to be used at home, a lengthy measurement might deter the user from using the device, which therefore undermines the very reason for that device.

SUMMARY

An aspect of the present invention is aimed at solving the previous limitation, by notably shortening the duration of the measurement.

In particular, optimization of each step of the method disclosed in the sudoscan documents have led to a decrease in time of the ESC process, as already observable on scale "Withings Body Comp". However, this optimization has opened a new field of exploration, among which the stabilization of the electro-chemical reactions at the electrodes.

Indeed, those reactions obey a specific kinetic and do not occur instantaneously. However, the method disclosed in the sudoscan documents is not particularly timely constrained and the measurement may easily take more than 30 s.

For a bathroom scale, the shorter the measurement's duration the better, as the engagement and the retention of the bathroom scale highly depend on it.

The inventors have therefore come up with an elegant solution, which is defined by the claims.

The present description relates to a method to evaluate an ESC value of a user body.

In an embodiment, the present description relates to a method to evaluate an electrochemical skin conductance, ESC, of a user body using a measurement device, the measurement device comprising:

- a pair of electrodes comprising an anode and a cathode configured each to be in contact with the user body (e.g., feet or hands),
- a direct voltage source configured to apply a direct voltage to the anode or the cathode wherein a value of the direct voltage is variable,
- a measurement resistor configured to determine a current value flowing through the used body, wherein an electrical resistance value of the measurement resistor is variable amongst a predetermined range,
- control circuitry configured to set the electrical resistance value of the measurement resistor and to set the value of the direct voltage, wherein the method comprises, by the control circuitry:

- pre-stabilizing during a pre-stabilizing period, the pre-stabilizing comprising:
- setting the electrical resistance value of the measurement resistor at a pre-stabilization value,
- applying a pre-stabilization voltage at the anode or the cathode (e.g., the anode) during the pre-stabilizing period,
- measuring during a measurement period following the pre-stabilization period, the measuring comprising:
- applying at least one measurement voltage at the anode,
- generating ESC values using at least one voltage measurements at the anode and/or the cathode obtained during the measurement period.

By adding a pre-stabilization period, the measurement method allows to, counterintuitively, reduce significantly the length of the measurement period as the need to stabilize the electrochemical reactions at the electrodes during the measuring decreased. All in all, the total duration of the ESC evaluation method may be significantly decreased.

In that regard, in an implementation, the pre-stabilization period is longer than each stabilization of the measurement period. For example, the pre-stabilization period lasts for at least 3 s.

In an embodiment, the measurement resistor is connected between the cathode and a reference voltage.

In an embodiment, the control circuitry sets the pre-stabilization value of the electrical resistance value of the measurement resistor amongst the lower 50%, or even the lower 25% of the predetermined range This pre-stabilization value is set and maintained during the whole duration of the pre-stabilization period.

More precisely, the pre-stabilization value of the measurement resistor may be chosen amongst the lower 10%, or is the lowest value, of the predetermined range.

The pre-stabilization value of the measurement resistor is predetermined, which means that the pre-stabilization value is the same regardless of the user.

In an embodiment, the predetermined range is between 3 k Ohms and 500 k Ohms, or between 9.6 k Ohms and 300 k Ohms. The predetermined range may include a plurality of discrete values, wherein the plurality is comprised between 4 and 32, for example between 4 and 16 and for example 8.

In an embodiment, the method further comprises calibrating the measurement resistor, by the control circuitry during a calibration period, calibrating comprising:

varying the electrical resistance value of the measurement resistor, setting the electrical resistance value at a calibration value (based on a comparison between a voltage at the anode and a voltage at the cathode.

In an embodiment, the method further comprises, by the control circuitry:

measuring at least one voltage difference around the measurement resistor during the pre-stabilization period and, determining the duration of the pre-stabilization period using at least said at least one voltage difference.

In an embodiment in which the measurement resistor is connected to the cathode, control circuitry measures the voltage value at the cathode.

In an embodiment, control circuitry is configured to determine that the evolution of the voltage value is below a predetermined threshold.

In an embodiment, the method further comprises, by the control circuitry:

determining at least one current value flowing through the user body using at least one voltage difference and the pre-stabilization value, determining the duration of the pre-stabilization period using at least the current value.

More specifically, the current value is determined by dividing the at least one voltage difference with the pre-stabilization value of the electrical resistor.

In an embodiment, the method further comprises, by the control circuitry:

computing the integral of the at least one current value since the beginning of the pre-stabilization period, determining the duration of the pre-stabilization period is determined using at least said integral.

In an embodiment, the duration of the pre-stabilization period is the shortest between:

X seconds, wherein X is comprised between 5 and 15 s, for example between 7 s and 12 s, for example between 8 s and 10 s, and the period of time for which said integral reaches a predetermined threshold.

In an embodiment, the pre-stabilization period lasts for a minimum duration, said minimum duration being at least 2 s, or even 4 s.

The pair of electrodes may be made of indium tin oxide, which is counterintuitive as stabilization is slower with ITO than with stainless steel, usually used in ESC evaluation method.

In an embodiment, the calibration period follows the pre-stabilization period. This allows to minimize the number of switch activations. As pre-stabilizing is carried out before calibrating, the electro-chemical equilibrium is already reached for the calibration and the value of the calibration resistor needs not be changed for the measurement method.

In an embodiment, the plurality of different measurement voltages includes between 3 and 6 voltage steps and each step lasts between 100 ms and 700 ms, for example between 200 ms and 500 ms.

In an embodiment, the measurement device includes a weight sensor. In an embodiment, the measurement device includes a measurement plate on which the pair of electrodes is placed.

The disclosure also relates to a measurement device to evaluate an electrochemical skin conductance (ESC) of the feet of a user, comprising:

a pair of electrodes comprising a first electrode and a second electrode configured each to be in contact with the user body, a direct voltage source configured to apply a direct voltage to the anode or the cathode, wherein a value of the direct voltage is variable, a measurement resistor configured to determine a current value flowing through the user body, wherein an electrical resistance value of the measurement resistor is variable amongst a predetermined range, control circuitry configured to set the electrical resistance value of the measurement resistor and to set the value of the direct voltage, wherein the control circuitry is configured to perform any of the methods disclosed above.

The disclosure also relates to a non-transitory computer readable medium comprising a computer program comprising instructions that, when performed by a processor of a measurement device, perform any of the methods disclosed above. The product computer program may be sent from a server to a measurement device to trigger an update of said measurement device.

BRIEF DESCRIPTION OF THE DRAWINGS

These features and benefits of the invention will appear more clearly upon reading the following description, provided solely as a non-limiting example, and done in reference to the appended drawings, in which.

DETAILED DESCRIPTION

Figure 1:
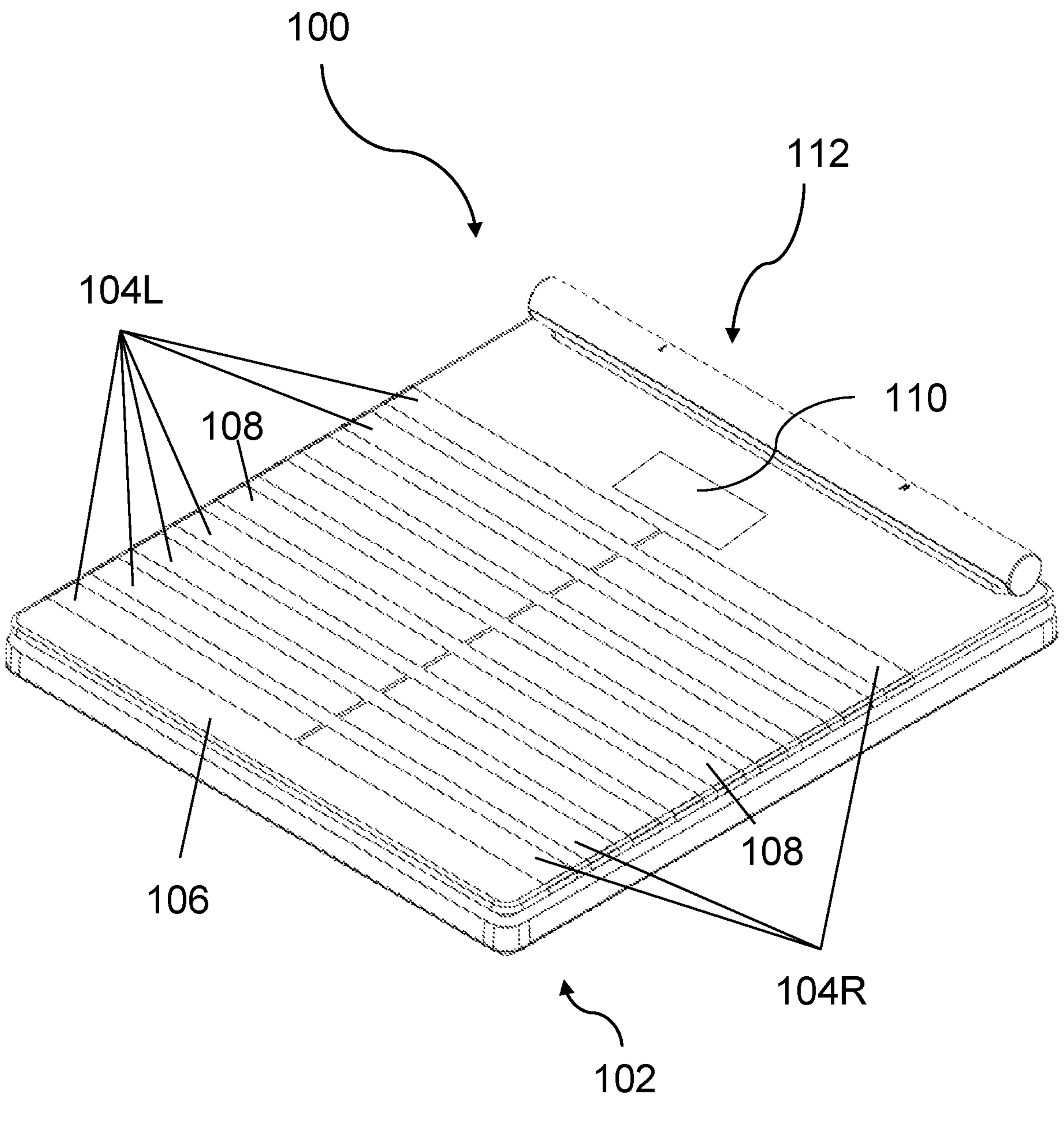
FIG. 1 shows a tridimensional representation of a measurement device according to an embodiment of the disclosure.

FIG. 1 illustrates a measurement device 100 configured to evaluate an electrochemical skin conductance value, referred to as ESC value, of a user. This measurement device 100 is disclosed in further detail in document FR2114739 filed on 31 Dec. 2021. The previously cited sudoscan documents disclosed another example of a measurement device.

The measurement device 100 comprises a base 102 on which the user may stand with his feet. The base 102 resembles a body scale. As illustrated on FIG. 1, the measurement device 100 may be an electronic bathroom scale, or personal scale, on which a user can position himself or herself to notably measure his or her weight. The measurement device 100 is configured to measure weights, for example in the range between 5 kg and 300 kg, in particular within the range between 30 kg and 200 kg. Even such a device is known as "bathroom scale", it may be used in a bedroom or in another room of a house. In an embodiment, the measurement device 100 may also be configured to measure a body composition, an electrocardiogram (ECG), a Pulse Wave velocity, a ballistocardiogram (BCG), etc.

The measurement device 100 includes a pair of electrodes 104L, 104R configured to be respectively in contact with the left foot and the right foot of the user. The pair of electrodes 104L, 104R may be located on a measurement plate 106, configured to receive the feet of the user. Therefore, to evaluate an ESC value, in an implementation, all the user needs to do is to stand on the measurement plate 106 and wait for a few seconds to let an ESC evaluation method be performed by the measurement device 100.

In a variation, the measurement device 100 also includes at least one additional electrode 108, called reference electrode. In the example of FIG. 1, all the electrodes on the base 102 includes strips. Some of the strips may be the electrode 104L, 104R, while other strips may be the reference electrode 108. The reference electrode is connected to a high-impedance component, namely a resistor with a high resistance value, so that the current escaping the body through the reference electrode is negligible. More details about this configuration may be found in document FR2114739.

To display information, the base 102 may include a display 110 (e.g., a screen).

Handle 112

In an embodiment, the measurement device 100 may comprise a handle 112, configured to be gripped by at least one hand of the user. The handle 112 is connected to the base via a cable (not illustrated). The handle 112 may include the reference electrode (not visible on the drawings). Again, more details about this configuration may be found in FR2114739.

Instead of a handle, a hand device may be used, as disclosed in the sudoscan documents.

In a variation, the handle may include the pair of electrodes used for the ESC measurement. The reference electrode may thus be on the base 102.

ESC Measurement

Figure 2:
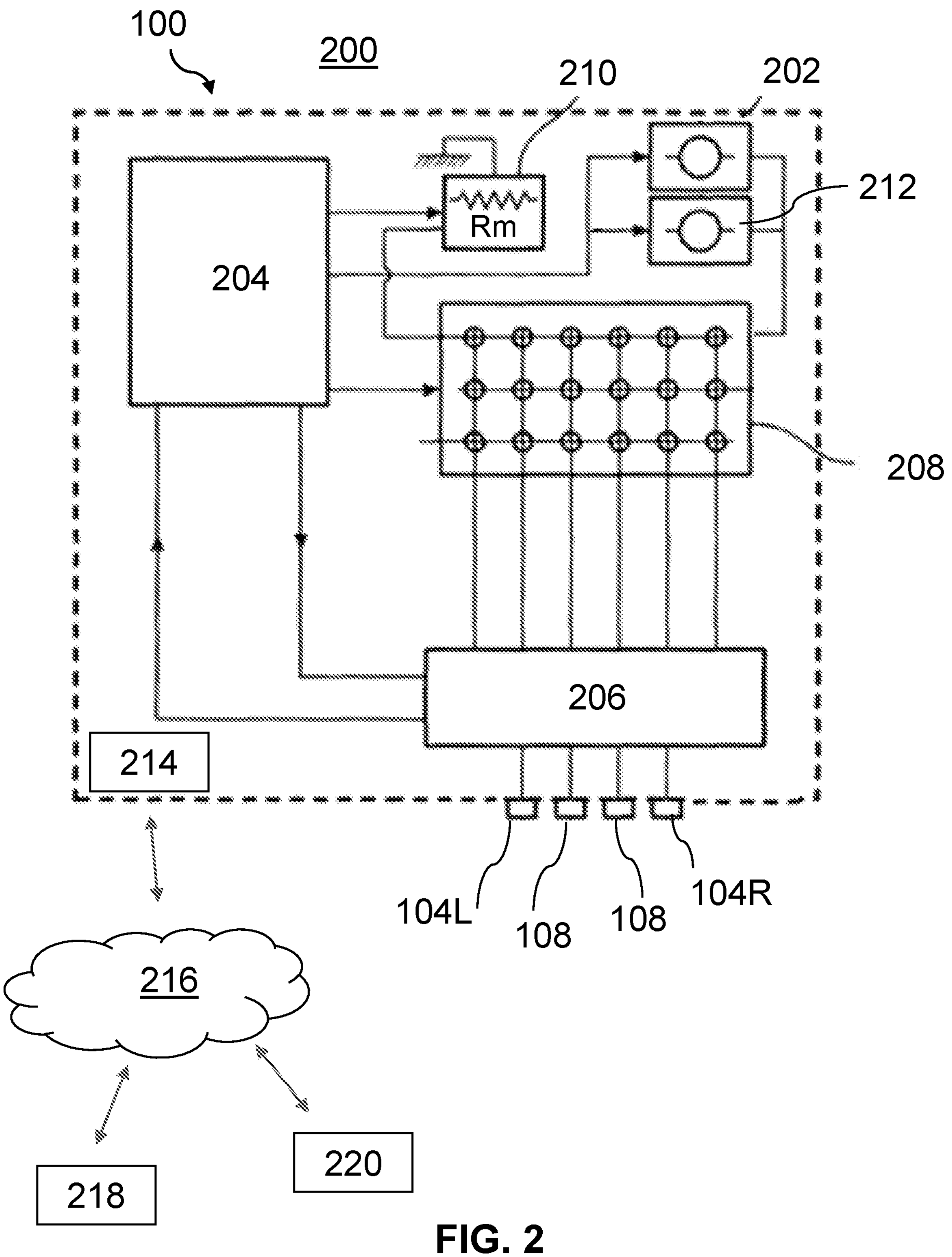
FIG. 2 shows a schematic representation of components of a measurement device according to an embodiment of the disclosure.
Figure 3:
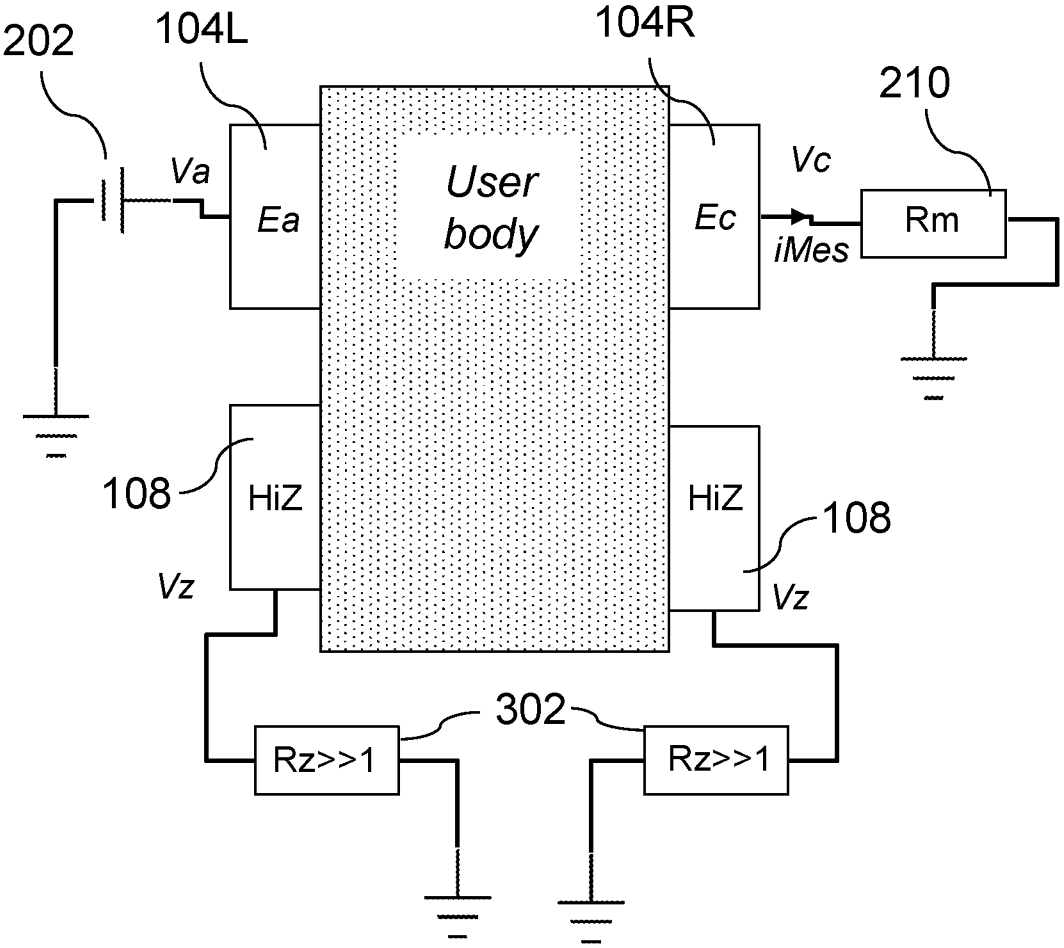
FIG. 3 shows a simplified schematic representation of some components of the measurement device and a user body.

FIG. 2 illustrates a schematic representation 200 of the measurement device 100. FIG. 3 illustrates some parts of the measurement device 100 in relation to a user body (e.g., the feet only, the hands only, the feet and the hands).

For the ESC measurement, the measurement device 100 includes a direct excitation source 202, such as a direct voltage source. The direct excitation source 202 may be connected to either one of the electrodes 104L, 104R of the pair of electrodes, which is thus called the anode Ea. The other electrode of the electrodes 104L, 104R which is not connected to the direct excitation source 202 is called the cathode Ec. For clarity reasons, in the present description and illustrations, the anode is the "first electrode 104L" and the "second electrode 104R" is the cathode Ec.

The measurement device 100 further includes control circuitry 204. Control circuitry 204 may include a processor and memory storing instructions for the processor. For example, the instructions are machine executable instructions, which when they are executed by the processor, perform one or more functions, method/process steps and/or procedures of the measurement device, including for example one or more, or all, of the steps of the methods of FIGS. 4, 6 and 7 described hereinafter. For example, the machine executable instructions are instructions to perform the method to evaluate an electrochemical skin conductance, ESC, of a user body using a measurement device as described herein. Control circuitry 204 may also include an analog to digital converter (ADC) and a digital to analog converter (DAC).

Measurement device 100 may also include at least one voltage sensor 206, configured to measure a voltage value. Voltage measured at the cathode Ec is referred to as Vc. The voltage sensor may be integrated in an Analog Front End (AFE).

The control circuitry 204 is configured to control the direct excitation source 202, that is to say to send a voltage instruction to the direct excitation source 202. For example, the voltage instruction may be for a constant direct voltage or for a series of decreasing steps. Voltage at the anode Ea is referred to as Va. This voltage usually corresponds to the instructed voltage to the direct excitation source 202.

The measurement device 100 includes a commutator 208 configured to switch some electrical connections between the electrodes and other elements. In a particular implementation, the commutator 208 may invert the anode Ea and the cathode Ec on the pair of electrodes 104L, 104R. The commutator 208 may have further functions, as presented in document FR2114739, for bioimpedance analysis for example.

HiZ Electrode

For the ESC measurement, the body may be in contact with the reference electrode 108, called electrode HiZ, to know the potential of the body and then enable to measure an ESC value at the right foot (or hand) and the left foot (or hand). This is extensively disclosed in the sudoscan documents.

For example, the HiZ electrode may be one electrode of the handle 112 or a third electrode on the plate 106. In an implementation, one of the strips may be the HiZ electrodes. In another implantation, two of the strips may be the HiZ electrode (one under each foot).

Measurement Resistor

To measure an ESC value, the measurement device 100 also includes a measurement resistor 210 configured to compute a current value flowing through the body. In an embodiment, the measurement resistor 210 is connected between a reference voltage (e.g., ground voltage of the control circuitry 204) and one electrode of the pair of electrodes, e.g., that which is not connected to the direct excitation source 202, i.e. the cathode Ec. The commutator 208 may be used to switch the connection between the measurement resistor 210 and the first electrode 104L or the second electrode 104R to switch from an anode/cathode configuration to a cathode/anode configuration.

Other configurations are possible, as long as a voltage difference around the measurement resistor 210 may be determined and a voltage difference relative to the user body may be determined.

The measurement resistor 210 has an electrical resistance value Rm known from the control circuitry 204. The electrical resistance value Rm is variable among a predetermined range and may be changed by the control circuitry 204. In an implementation, the predetermined range goes from 3 k Ohms to 500 k Ohms or even between 9.6 k Ohms and 300 k Ohms. The measurement resistor 210 may include an array of resistors connected together with switches, so that to the predetermined range is constituted by a plurality of discrete values. The switches may be operated by the control circuitry 204. In an implementation, the plurality is comprised between 4 and 32, even between 4 and 16, and may be 8. Using a voltage value of the cathode Ec, called Vc, and the electrical resistance value Rm, control circuitry 204 may determine a current iMes flowing through the user body. Conversely, as the reference electrode 108 is high impedance, the current therein is negligible, therefore generating no loss.

Alternative Excitation Source

For other measurements also using inter alia the electrodes 104L, 104R, the measurement device 100 may include an alternative excitation source 212 configured to generate an alternative current. The alternative excitation source 212 may be used for bioimpedance (fat mass, impedance plethysmography, etc.), as described in detail in document FR2114739. To steer the alternative current to the appropriate electrodes and to measure a voltage value at the appropriate electrodes, the commutator 206 is activated.

Connected Measurement Device

The measurement device 100 may include a wireless module 214 to send and receive data from a communications network 216, which may be hybrid (wireless, wired, such as BLUETOOTH® (a short-range wireless technology standard), Wi-Fi, Ethernet, etc.). Those data may be received from or sent to a remote server 218 and/or to a personal mobile phone 220 (e.g., smartphone, tablet, etc.). For example, the ESC values may be sent by the control circuitry 204 to the server 218, which then forwards those data to the personal mobile phone 220.

Other Sensors

The measurement device 100 may include a weight sensor (not illustrated) and/or impedance sensors (for example using the pair of electrodes 104L, 104R and at least another pair of electrodes on the measurement plate 102 and/or the handle) coupled with the alternative excitation source 202.

Materials of the Electrode

The electrodes 104L, 104R may be made of stainless steel, titanium, brass, nickel or an alloy thereof, or even conductive plastics. In a specific embodiment, the electrodes 104L, 104R are made of indium tin oxide, known as ITO. ITO has different properties from stainless steel which favors electro-chemical reactions compared to ITO.

The electrodes 104L, 104R may be a coating on the measurement plate 106.

In an embodiment, the coating is made of and the measurement plate 106 is made of glass.

How to Obtain an ESC Value

More details may be found in the sudoscan documents but the general principle will be described here below. As mentioned previously, in the following description, the first electrode 104L is the anode Ea and the second electrode 104R is the cathode Ec. However, thanks to the commutator 208, the first electrode 104L may be the cathode Ec and the second electrode 104R may be the anode Ea.

FIG. 3 illustrates a simplified representation of a user on the measurement system. The user is represented in dots as the "user body". The left foot (or hand) may be in contact with the first electrode 104L which is the anode Ea, connected to the direct excitation source 202. The right foot (or hand) may be in contact with the second electrode 104R which is the cathode Ec, connected to the measurement resistor 210. Each foot (or hand) may also be connected to a reference electrode 108, which is the HiZ electrode, whose impedance is high thanks to one or more resistors 302. A measurement device without the reference electrodes 108 is also possible.

Measurement Method

Figure 4:
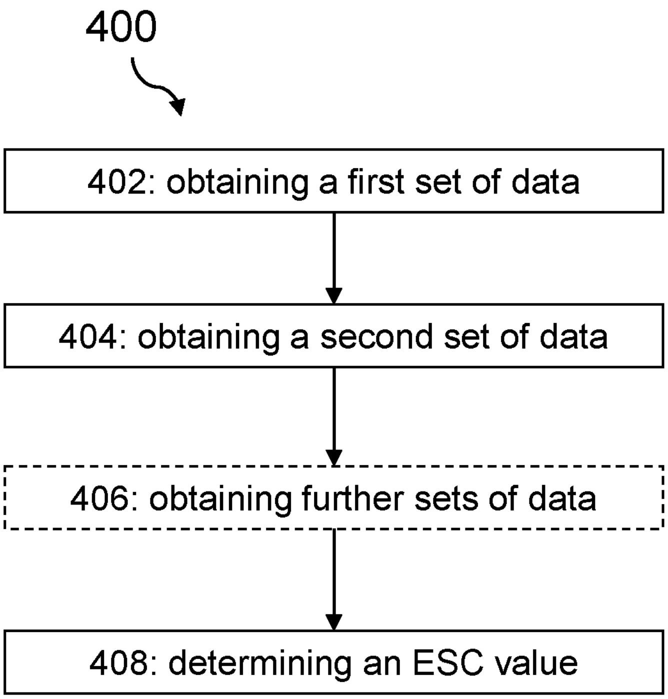
FIG. 4 shows a measurement method to obtain ESC values.

FIG. 4 illustrates a measurement method 400 to measure an ESC value, performed during a measurement period. This calibration method is carried out after a pre-stabilization method. In addition, a calibration method of the electrical resistance value Rm of the measurement resistor 202 may be performed before the measurement period. The pre-stabilization method and the calibration method will be described in detail later.

The pre-stabilization is aimed at reaching a state in which the electro-chemical reaction occurring at the anode Ea and the cathode Ec are stabilized.

The calibration is aimed at setting the electrical resistance value Rm at an appropriate value, called calibration value Rcalib for acceptability ranges of the electronic components of the control circuitry 204.

Control circuitry 204, at 402, applies a first measurement voltage Va1 at the anode Ea using the direct excitation source 202 and obtain a first measured voltage Vc1 at the cathode Ec, using the voltage sensor 206.

Control circuitry 204 may, at 404, in similar manner to 402, apply a second measurement voltage Va2 at the anode Ea and obtain a second measured voltage Vc2 at the cathode Ec. The second measurement voltage Va2 is different from the first measurement voltage Va1. Steps 402 and 404 are distinct and usually follow each other.

The applied voltages Va at the anode Ea may be comprised between 0 and 5V, for example between 1V and 4V.

With the information of the measured voltage Vc and the electrical resistance value Rm, the control circuitry 204 may determine a measured current value iMes flowing through the user body. Therefore using data of step 402 and 404, control circuitry 204 may obtain two sets of data: (Va1; Vc1; iMes1) and (Va2; Vc2; iMes2).

Other measured voltage may be used, as long as a voltage difference in the body user may be obtained and a voltage difference around the resistor may be determined. For example, instead of Va, control circuitry 204 may obtain Vc or Vz (Vz being the voltage value of the HiZ electrode) and instead of Vc, control circuitry 204 may obtain Va or Vz. In this implementation, as the measurement resistor 210 is connected to the anode, Vc is needed to determined the current flowing through the measurement resistor 201.

Control circuitry 204 may generate, at 406, further sets of data using different voltages values (dashed lines on FIG. 4). For example, one additional set of data is generated.

Control circuitry 204 determines, at 408, an ESC value, using the sets of data of 402 and 404 (and 406 if applicable).

More specifically, determining the ESC value may be broken down as follows. Control circuitry 204, may compute a voltage difference using any two of Va, Vc, Vz (Vz being the voltage value of the HiZ electrode) and may determine a linear regression between at least two points comprising each said voltage difference and the associated measurement current value iMes. As illustrated on FIG. 5, control circuitry 204 computes ΔV1=Va1−Vz and ΔV2=Va2−Vz and determines the slope of the linear regression linreg between (ΔV1; iMes1) and (ΔV2; iMes2) (and other points, if any). The slope is representative of the ESC value of the user. To get more precise results, more than two points may be used for the linear regression, as illustrated on FIG. 5. However, only the last few sets of data may be used to determine the ESC value (e.g., the last 3).

Figure 5:
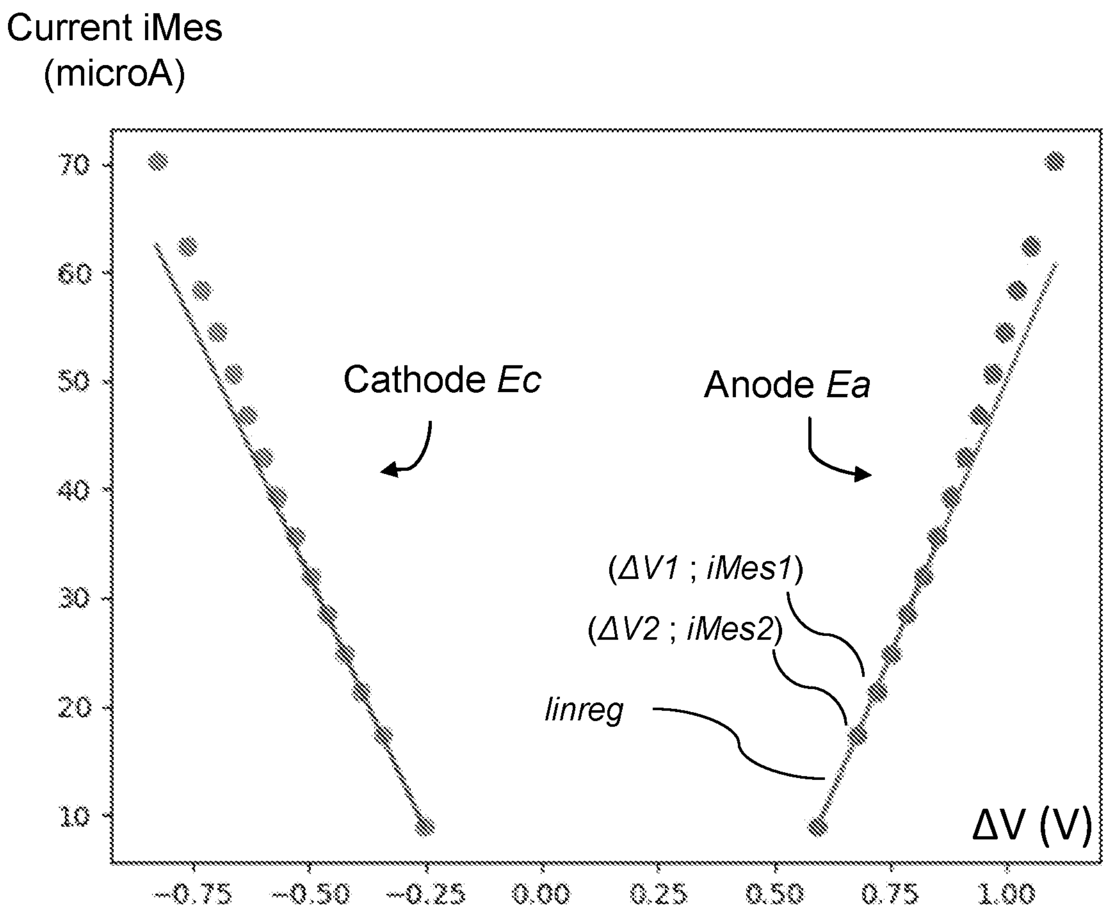
FIG. 5 shows a graph illustrating how ESC values may be determined.

Measurement method 400 may be carried a second time with an anode-cathode inversion, to build the second curve on FIG. 5 and the average of the slope may be carried out.

In particular, Va-Vz allows to have the ESC value of one foot (the left foot here as the left foot is contacted the anode Ea), while Vc-Vz allows to have the ESC value of the other foot (the right foot here as the right foot is contacted the cathode C).

Control circuitry 204 may compute averages of those ESC values to output a single ESC value.

For example, control circuitry 204 may apply direct voltage steps of decreasing value. Each step may last between 300 ms and 5 s, for example between 300 ms and 700 ms to reduce the length of the ESC measurement. In particular, this reduced duration is permitted by the pre-stabilization method that will be disclosed later.

In an implementation, only the last X % of the voltage steps may be used to determine the ESC value. This lets the first 100%-X % of the voltage steps help the electrochemical reaction to stabilize, in addition to the pre-stabilization method. X may be between 30 and 5, for example around 10.

Calibration Method 600

The calibration method is performed by the control circuitry 204 and one example is disclosed in the sudoscan documents.

The goal of the calibration is to set the electrical resistance value Rm of the measurement resistor 210 to a value, called calibration value Rcalib, enabling an effective acquisition by the electronics components of the measurement device 100. In that regard, it is desired to keep the voltage Vc (the voltage value at the cathode Ec) at a fraction of Va (the voltage value at the anode Ea). More precisely, the calibration value Rcalib may be set by the control circuitry 204 so that $0.1Va<Vc<0.9$ Vc. In a specific embodiment, the control circuitry 204 set the electrical resistance value Rm so that $0.4Va<Vc<0.6Vc$. In this implementation, the calibration value Rcalib is roughly equal to the electrical resistance value of the user body. In a more general definition, Rcalib is chosen based on a comparison between Va and Vc.

Figure 6:
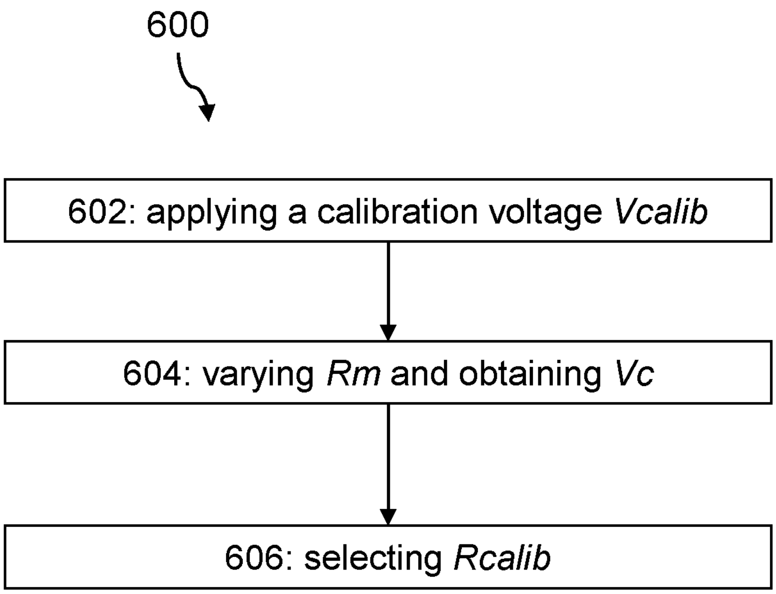
FIG. 6 shows a pre-stabilization method.

To identify an appropriate calibration value Rcalib, control circuitry 204 may apply a calibration method 600, illustrated on FIG. 6.

Control circuitry 204, at 602, applies a calibration voltage Vcalib at the anode Ea with the direct excitation source 202 and, at 604, varies the electrical resistance value Rm of the measurement resistor 210. Vcalib is a fixed value. In parallel, control circuitry 204, at 604 too, obtains the voltage Vc at the cathode Ec for each electrical resistance value Rm.

Control circuitry 204 selects, at 606, a calibration value Rcalib as one of the values that fits one of the previous criteria regarding Va and Vc, and more particularly one of the values for which Vc is the closest to Va/2. The selected calibration value Rcalib is stored by the control circuitry 204.

This method was described in WO2008/107324 (pages 13 and 14).

At the end of the calibration method 600, control circuitry 204 has obtained the appropriate electrical resistance value Rm, called Rcalib, to measure an ESC value as disclosed in measurement method 400.

The calibration voltage may be comprised between 1V and 5V. The calibration period may last between 300 ms and 2 s.

Pre-Stabilization Method 700

Figure 7:
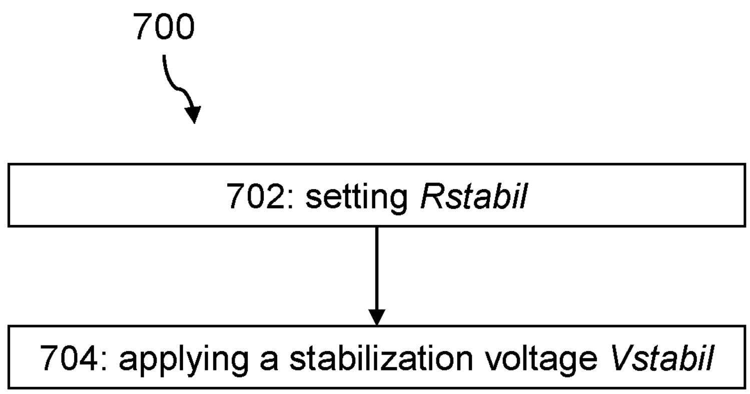
FIG. 7 shows a calibration method.

FIG. 7 illustrates a pre-stabilization method 700 carried out by the control circuitry 204.

The pre-stabilization method 700 is performed during a pre-stabilization period, carried out before the measurement period of the measurement method 400. In other words, this allows to drastically shorten each voltage steps at 402 and 404. This allows to drastically shorten the measurement method 400, as each voltage step may be shortened.

This pre-stabilization period thus works as an additional stabilization period, as each beginning of each voltage step may be considered as a stabilization period. This additional pre-stabilization period, which adds some duration to the ESC evaluation value (all things being equal), allows to actually shorten each stabilization period of the voltage steps. Therefore, the pre-stabilization period lasts longer than each stabilization period of the voltage steps, notably lasts longer than each voltage step. In an embodiment, the pre-stabilization period lasts longer than the sum of all the stabilization periods of the voltage steps. This counter-intuitive approach has greatly improved the ESC evaluation flow for the user.

More particularly, control circuitry 204, at 702, sets the electrical resistance value Rm of the measurement resistor 210 at a pre-stabilization value Rstabil, and, at 704, applies a pre-stabilization voltage Vstabil at the anode Ea (first electrode 104L here) during a pre-stabilization period. During this pre-stabilization period, no measurements per se are carried out. Control circuitry 202 may monitor the voltage at the anode Va and at the cathode Vc but those voltage values will not be used to determine the ESC values of the human body.

The stabilization voltage may be between 2V and 5V, for example between 3V and 4V. More precisely, the stabilization voltage Vstabil may be equal to the calibration voltage Vcalib.

Low Pre-Stabilization Value Rstabil

To accelerate the kinetics of the electrochemical reactions occurring at the anode Ea and the cathode Ec, the inventors have come up with an elegant solution involving an increase of the current iMes flowing through the user body. To that end, the inventors implemented a solution in which the pre-stabilization value Rstabil is set as low during the pre-stabilization method 700. In striking contrast with the sudoscan documents, in which the electrical resistance value was set at the calibration value Rcalib for the stabilization at east voltage step, here the pre-stabilization value Rstabil is generally lower than the calibration value Rcalib, if not always lower. As a reminder, the calibration value Rcalib depends on the user and varies amongst a predetermined range, such as 3 k Ohms and 300 k Ohms.

More concretely, control circuitry 204 may, at 602, sets the pre-stabilization value amongst the lower 50% of the predetermined range of the electrical resistance value of the measurement resistor 210. To further increase the current iMes, it could even be the 25% of the predetermined range, or even the 10%. In an implementation, to maximize the current iMes, the pre-stabilization value Rstabil is the lowest value of the predetermined range. One consequence is that the calibration value Rcalib is necessarily equal or greater than the pre-stabilization value Rstabil. For a predetermined range that includes 8 values for Rm, the lower 25% means the 2 lowest values and the 10% amounts to the lowest value.

To simplify the pre-stabilization method, the pre-stabilization value Rstabil of the measurement resistor 210 is predetermined. This means that the pre-stabilization value Rstabil is set regardless of the user body. As mentioned previously, the predetermined pre-stabilization value Rstabil is the lowest value of the predetermined range.

For example, the lowest value may be 5 k Ohms in a range going from 5 k Ohms to 300 k Ohms.

To ensure that a pre-stabilization method 700 with a long enough pre-stabilization period is applied to any user body, the control circuitry may set a minimum duration comprised between 2 s and 5 s, such as between 3 s and 5 s.

In an embodiment, the pre-stabilization method 700 is carried out before the calibration method 600. This enables to easily have a pre-stabilization value Rstabil of the measurement resistor 210 that is different from the calibration value Rcalib of the measurement resistor 210, in particular a pre-stabilization value Rstabil lower than a calibration value Rcalib. This allows to increase the current iMes and accelerate the electrochemical reactions occurring at the anode Ea and the cathode Ec.

In an embodiment, the pre-stabilization method 700 is carried out after the calibration method 600. In that case, the pre-stabilization value Rstabil of the measurement resistor 210 may be the calibration value Rcalib of the measurement resistor 210 but without the benefit of a higher current, as the calibration value Rcalib is not amongst the lower values of the predetermined range. In alternate embodiment, control circuitry 2014 may carry out the calibration method 700 and then, for the pre-stabilization method 700, set the pre-stabilization value as defined in the pre-stabilization method 700 described above. For the measurement method 600, control circuitry 204 sets the electrical resistance value Rm back to the calibration value Rcalib. A few switchings are involved but the overall duration of the ESC evaluation method is not increased.

Adaptive Duration of the Pre-Stabilization Period

In an embodiment, the duration of the pre-stabilizing period is predetermined, with a fixed value, such as 9s. However, the inventors have also noticed that the time to pre-stabilize the electrochemical reactions at the anode Ea and the cathode Ec may vary upon the user bodies and more particularly upon the neurologic state of the user body. For example, someone not suffering from a neuropathy may pre-stabilize quickly (e.g., less than 5 s) while someone suffering from a neuropathy may pre-stabilize slowly (e.g., more than 6 s).

Therefore, to optimize the duration of the pre-stabilization period, control circuitry may be configured to measure, during the pre-stabilization period, at least one voltage value Vc at the cathode Ec and to determine the duration of the pre-stabilization period using at least said at least one voltage value Vc.

In an embodiment, control circuitry 204 computes the evolution of the voltage value Vc at the cathode Ec (e.g., a derivative or a discrete derivative) and determines that this evolution is below a predetermined threshold. In other words, the kinetic speed of the electrochemical reaction has decreased, hereby meaning it has stabilized. By below, it is meant in terms of absolute value (positive number).

In an embodiment, control circuitry 204 determines at least one current value of the current flowing the user body. To that end, control circuitry uses the voltage value Vc at the cathode Ec and the pre-stabilization value Rstabil of the measurement resistor 210. Further, control circuitry 204 determines the duration of the pre-stabilization period using at least the current value iMes. The current value iMes is representative of the kinetics of the electrochemical reactions and therefore provides some information about the state of the stabilization of the electrodes Ea, Ec.

The current value iMes is determined by dividing the voltage value Vc at the cathode Ec (or its difference with the reference voltage) with the pre-stabilization value Rstabil of the measurement resistor 210.

In a specific implementation of this embodiment, the control circuitry 204 may compute the integral of the at least one current value iMes since the beginning of pre-stabilizing period (e.g., a discrete integral or summation, the precision of which depending on the number of current values iMes) and may determine the duration of the pre-stabilization period using said integral. This integral represents the cumulated number of charged particles that flowed through the user body.

In an implementation, the pre-stabilization period ends when the integral reaches a predetermined threshold, which amounts to a predetermined number of electric particles flowing through the user body.

An upper limit may be applied however, to avoid having a pre-stabilization period that lasts too long when the predetermined threshold is not reached quickly enough. Therefore, control circuitry 204 may end the pre-stabilization after a time limit of X seconds. Therefore, the pre-stabilization method 700 ends when the elapsed time since the beginning of the pre-stabilization period reaches the time limit, regardless of the value of the integral. X may be comprised between 5 s and 15 s, for example between 7 s and 12 s, and even for example between 8 s and 10 s. For a user body with no neuropathy, the integral reaches the predetermined threshold before the elapsed time reaches the time limit. For a user body suffering from severe neuropathy, the elapsed time reaches the time limit before the integral reaches the predetermined threshold. However, the predetermined threshold is chosen so that to obtain a sufficient quality of ESC measurement in any case.

EXAMPLES

Figure 8:
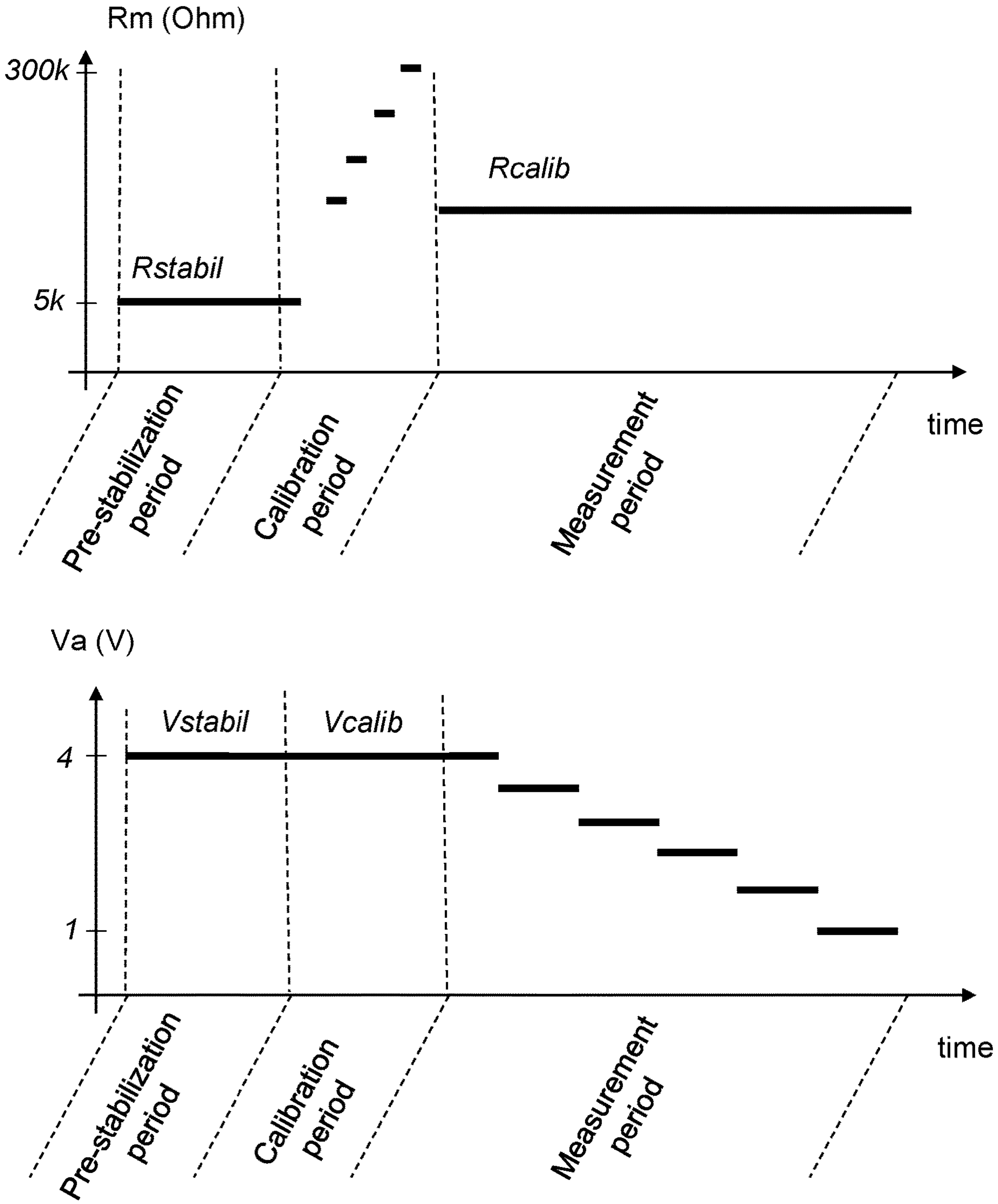
FIG. 8 shows a timeline of an ESC evaluation method with a pre-stabilization period, a calibration period and a measurement period.

FIG. 8 illustrates an embodiment of an evaluation method including, in that following order: the pre-stabilization method 700, the calibration method 600 and the measurement method 400 (no accurate scale and durations for the resistance, the voltage and the time on FIG. 8).

The top graph shows the electric resistance value Rm of the measurement resistor 210 over time during the pre-stabilization period, the calibration period and the measurement period and the bottom graph shows the voltage Va at the anode Ea over time during the pre-stabilization period, the calibration period and the measurement period.

As disclosed previously, during the pre-stabilization method 700, the resistance value Rm is set to the pre-stabilization value Rstabil, as one of the low values of the predetermined range, then during the calibration method 600, the resistance value Rm is varying to identify the calibration value Rcalib. In most cases, Rcalib is different from Rstabil, as Rstabil is for example a predetermined value for all users (e.g., the lowest possible value of Rm), while Rcalib depends on the user body.

In an implementation, at the anode Ea, the pre-stabilisation voltage Vstabil is the same as the calibration voltage Vcalib. During the measurement method, the voltage Va varies as descending steps.

In this embodiment, the measurement device 100 is already (or at least partially) stabilized for the calibration method 600.

Another variation of the evaluation method may temporally invert the calibration period and the pre-stabilization period. In that respect, when the calibration method 600 implies decreasing values of the electrical resistance value Rm of the measurement resistor 210, the last electrical resistance value of the calibration method 600 may be the lowest value of the predetermined range. In that case, the predetermined value for the pre-stabilization value Rstabil is the same lowest value, to avoid one additional switching of the measurement resistor 210. However, the calibration method may imply increasing values of the electrical resistance Rm, as illustrated. In that case, the first electric resistance value Rm of the calibration method 600 may be the lowest possible value, which is, in an implementation, the calibration value Rcalib.

The articles “a” and “an” may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

It will be appreciated that the various embodiments and aspects of the inventions described previously are combinable according to any technically permissible combinations.

The invention claimed is:

1. A method to evaluate an electrochemical skin conductance, ESC, of a user body using a measurement device, the measurement device including a pair of electrodes comprising an anode and a cathode configured each to be in contact with the user body, a direct voltage source configured to apply a direct voltage to the anode, wherein a value of the direct voltage is variable, a measurement resistor configured to determine a current value flowing through the user body, wherein an electrical resistance value of the measurement resistor is variable amongst a predetermined range, and control circuitry configured to set the electrical resistance value of the measurement resistor and to set the value of the direct voltage, the method comprising, by the control circuitry:

pre-stabilizing during a pre-stabilizing period, the pre-stabilizing comprising:

setting the electrical resistance value of the measurement resistor at a predetermined pre-stabilization value, which is the same regardless of the user, wherein the control circuitry sets the pre-stabilization value amongst a lower 50% of the predetermined range, applying a pre-stabilization voltage at the anode during the pre-stabilizing period, calibrating the measurement resistor, by the control circuitry during a calibration period following the pre-stabilizing period, the calibrating comprising:

varying the electrical resistance value of the measurement resistor, and setting the electrical resistance value at a calibration value based on a comparison between a voltage at the anode and a voltage at the cathode, and measuring during a measurement period following the calibration period, the measuring comprising:

applying at least one measurement voltage at the anode, and generating ESC values using at least one voltage measurement at the anode and/or the cathode obtained during the measurement period.

2. The method of claim 1, wherein applying at least one measurement voltage at the anode includes applying at least one voltage step, and wherein the pre-stabilizing period lasts longer than each voltage step.

3. The method of claim 1, wherein the control circuitry sets the pre-stabilization value of the electrical resistance value of the measurement resistor amongst the lower 25% of the predetermined range.

4. The method of claim 1, wherein the pre-stabilization value of the measurement resistor is chosen amongst the lower 10%, or is the lowest value, of the predetermined range.

5. The method of claim 1, wherein the predetermined range is between 3 kOhms and 500 kOhms.

6. The method of claim 1, wherein the electrical resistance value of the measurement resistor for the measuring is the calibration value.

7. The method of claim 1, further comprising, by the control circuitry:

measuring at least one voltage difference around the measurement resistor during the pre-stabilization period, and determining a duration of the pre-stabilization period using at least the at least one voltage difference.

8. The method of claim 1, further comprising, by the control circuitry:

determining at least one current value flowing through the user body using at least one voltage difference around the measurement resistor and the pre-stabilization value, and determining a duration of the pre-stabilization period using at least the current value.

9. The method of claim 8, further comprising, by the control circuitry:

computing an integral of the at least one current value since the beginning of the pre-stabilization period, and determining the duration of the pre-stabilization period using at least the integral.

10. The method of claim 9, wherein the duration of the pre-stabilization period is the shortest between:

X seconds, wherein X is comprised between 5s and 15s, a period of time for which the integral reaches a predetermined threshold.

11. The method of claim 10, wherein X is comprised between 7s and 12s.

12. The method of claim 1, wherein the pair of electrodes is made of indium tin oxide.

13. The method of claim 1, wherein the applying the at least one measurement voltage at the anode comprises applying between 3 and 6 voltage steps and each step lasts between 100 ms and 700 ms.

14. The method of claim 13, wherein each step lasts between 200 ms and 500 ms.

15. The method of claim 1, wherein applying the at least one measurement voltage at the anode comprises applying a plurality of voltage steps, each voltage step including a stabilization period, and wherein the pre-stabilization period lasts longer than a sum of the stabilization periods of the plurality of voltage steps.

16. The method of claim 1, wherein the pre-stabilization value is lower than the calibration value.

17. A measurement device to evaluate an electrochemical skin conductance (ESC) of the feet of a user, comprising:

a pair of electrodes comprising an anode and a cathode configured each to be in contact with the user's body, a direct voltage source configured to apply a direct voltage to the anode, wherein a value of the direct voltage is variable, a measurement resistor configured to determine a current value flowing through the user's body, wherein an electrical resistance value of the measurement resistor is variable amongst a predetermined range, control circuitry configured to set the electrical resistance value of the measurement resistor and to set the value of the direct voltage, wherein the control circuitry is configured to perform the method of claim 1.

18. A non-transitory computer readable medium storing a computer program comprising instructions that, when performed by a processor of a measurement device, perform the method of claim 1.

* * * * *